(12) United States Patent
Liu et al.

(10) Patent No.: US 7,456,225 B1
(45) Date of Patent: Nov. 25, 2008

(54) **LIVER PROTECTION COMPOUNDS OF THE CYCLOHEXENONE TYPE FROM *ANTRODIA CAMPHORATA***

(75) Inventors: Sheng-Yun Liu, Taipei Hsien (TW); Wu-Che Wen, Taipei hsien (TW); Mao-Tien Kuo, Taipei Hsien (TW)

(73) Assignee: Golden Biotechnology Corporation, Taipei Hsien (TW)

( * ) Notice: Subject to any disclaimer, the term of this patent is extended or adjusted under 35 U.S.C. 154(b) by 0 days.

(21) Appl. No.: 11/902,599

(22) Filed: Sep. 24, 2007

(30) Foreign Application Priority Data

Jun. 14, 2007 (TW) .............................. 96121548 A

(51) Int. Cl.
*A61K 31/12* (2006.01)
*C07C 49/543* (2006.01)
*C07C 49/557* (2006.01)

(52) U.S. Cl. ...................................... 514/690; 568/377

(58) Field of Classification Search ................. 568/377; 514/690

See application file for complete search history.

(56) References Cited

OTHER PUBLICATIONS

Lynn, "Development of insect cell lines: Virus susceptibility and applicability to prawn cell culture," Methods in Cell Science, vol. 21, 1999, pp. 173-181.

"Development of Animal Cell Populations In Vitro," pp. 91-113.

Goodwin et al., "Gypsy Moth Cell Lines Divergent in Viral Susceptibility: I. Culture and Identification," In Vitro, vol. 14, No. 6, 1978, pp. 485-494.

Summers et al., "A Manual of Methods for Baculovirus Vectors and Insect Cell Culture Procedure," Texas Agricultural Experiment Station No. 155, 198, pp. 14-16.

Wang et al., "Continuous Cell Line from Pupal Ovary of *Perina nuda* (Lepidoptera: Lymantriidae) That Is Permissive to Nuclear Polyhedrosis Virus from *P. nuda*," Journal of Invertebrate Pathology, vol. 67, 1996, pp. 199-204.

*Primary Examiner*—Sikarl A Witherspoon
(74) *Attorney, Agent, or Firm*—Birch, Stewart, Kolasch & Birch, LLP

(57) ABSTRACT

The present invention relates to a compound of *Antrodia camphorata* used for liver protection, in particular to an extract, 4-hydroxy-2,3-dimethoxy-6-methyl-5(3,7,11-trimethyl-dodeca-2,6,10-trienyl)-cyclohex-2-enone which is isolated from *Antrodia camphorata*. The cyclohexenone compound according to the invention helps to alleviate liver injury and fibrosis induced by chemicals and reduces the levels of alanine aminotransferase (ALT) and aspartate aminotransferase (AST). By increasing the contents of glutathione peroxidase (GSHPx) and catalase (CAT), cyclohexenone further decreases the liver damage and the oxidative pressure caused by free radicals, enhances the antioxidant ability and achieves the purposed of liver protection.

20 Claims, 5 Drawing Sheets
(3 of 5 Drawing Sheet(s) Filed in Color)

LIVER PROTECTION COMPOUNDS OF THE CYCLOHEXENONE TYPE FROM *ANTRODIA CAMPHORATA*

BACKGROUND OF THE INVENTION

1. Field of the Invention

The present invention relates to a liver protection compound, in particular to a cyclohexenone compound isolated and purified from *Antrodia camphorata* extracts, which can be applied in liver protection and alleviation of liver injury and fibrosis.

2. The Prior Arts

The liver is the largest and most complicated organ of metabolism in the body, which is responsible for metabolizing fats, carbohydrates, proteins, vitamins, hormones, and bile. Besides, it has abilities of secretion, excretion, biological transformation and the like. Liver is also an important barrier organ where the detoxification is important to protect the organism. Damaged liver function can cause impaired metabolism, which may affect the function of other organs or can lead to death when serious. The prevalence of liver diseases is quite high in Taiwan. According to the Department of Health in Taiwan, chronic liver disease and liver cirrhosis ranked the sixth among the top ten causes of death for Taiwan people, and caused more than 3000 death per year. The rate is still increasing. Therefore, development of liver protection substances, further to prevent or treat liver related diseases, is crucial at present.

*Antrodia camphorata* is also called Chang-Zhi, Niu Chang-Zhi, red camphor mushroom and the like, which is a perennial mushroom belonging to the order Aphyllophorales, the family Polyporaceae. It is an endemic species in Taiwan growing on the inner rotten heart wood wall of *Cinnamomum kanehirae* Hay. *Cinnamoum kanehirai* Hay is rarely distributed and being overcut unlawfully, which makes *Antrodia camphorata* growing inside the tree in the wild became even rare. The price of *Antrodia camphorata* is very expensive due to the extremely slow growth rate of natural *Antrodia camphorata* that only grows between Junes to October.

The fruiting bodies of *Antrodia camphorata* are perennial, sessile, hard and woody, which exhales strong smell of sassafras (camphor aroma). The appearances are various with plate-like, bell-like, hoof-like, or tower-like shapes. They are reddish in color and flat when young, attached to the surface of wood. Then the brims of the front end become little curled tilted and extend to the surroundings. The color turns to be faded red-brown or cream yellow brown, with ostioles all over. This region is of very high medical value.

In traditional Taiwanese medicine, *Antrodia camphorata* is commonly used as an antidotal, liver protective, anti-cancer drug. *Antrodia camphorata*, like general edible and medicinal mushrooms, is rich in numerous nutrients including polysaccharides (such as β-glucosan), triterpenoids, superoxide dismutase (SOD), adenosine, proteins (immunoglobulins), vitamins (such as vitamin B, nicotinic acid), trace elements (such as calcium, phosphorus and germanium and so on), nucleic acid, agglutinin, amino acids, steroids, lignins and stabilizers for blood pressure (such as antodia acid) and the like. These physiologically active ingredients are believed to exhibit effects such as: anti-tumor activities, increasing immunomodulating activities, anti-allergy, anti-bacteria, anti-high blood pressure, decreasing blood sugar, decreasing cholesterol, liver protection, anti-fatigue, and the like.

Triterpenoids are the most studied component among the numerous compositions of *Antrodia camphorata*. Triterpenoids are the summary terms for natural compounds, which contain 30 carbon atoms with the pent acyclic or hex acyclic structures. The bitter taste of *Antrodia camphorata* is from the component of triterpenoids. Three novel ergostane-type triterpenoids (antcin A, antcin B, antcin C) were isolated by Chiang et al. from the fruiting bodies of *Antrodia camphorata* (Cherng, I. H., and Chiang, H. C. 1995. Three new triterpenoids from *Antrodia cinnamomea*. J. Nat. Prod. 58:365-371). Three new compounds zhankuic acid A, zhankuic acid B and zhankuic acid were extracted from the fruiting bodies of *Antrodia camphorata* with ethanol by Chen et al. (Chen, C. H., and Yang, S. W. 1995. New steroid acids from *Antrodia cinnamomea*, —a fungus parasitic on *Cinnamomum micranthum*. J. Nat. Prod. 58:1655-1661). In addition, Cherng et al. also found three other new triterpenoids from the fruiting bodies of *Antrodia camphorata*, which are sesquiterpene lactone and 2 biphenyl derived compounds, 4,7-dimethoxy-5-methyl-1,3-benzodioxole and 2,2',5,5'-teramethoxy-3,4,3',4'-bi-methylenedioxy-6,6'-dimethylbiphenyl (Chiang, H. C., Wu, D. P., Cherng, I. W., and Ueng, C. H. 1995. A sesquiterpene lactone, phenyl and biphenyl compounds from *Antrodia cinnamomea*. Phytochemistry. 39:613-616). In 1996, four novel ergostane-type triterpenoids (antcins E and F and methyl antcinates G and H) were isolated by Cherng et al. with the same analytic methods (Cherng, I. H., Wu, D. P., and Chiang, H. C. 1996. Triteroenoids from *Antrodia cinnamomea*. Phytochemistry. 41:263-267). And two ergostane related steroids, zhankuic acids D and E together with three lanosta related triterpenes, 15 alpha-acetyl-dehydrosulphurenic acid, dehydroeburicoic acid, dehydrosulphurenic acid were isolated by Yang et al. (Yang, S. W., Shen, Y. C., and Chen, C. H. 1996. Steroids and triterpenoids of *Antrodia cinnamomea*—a fungus parasitic on *Cinnamomum micranthum*. Phytochemistry. 41:1389-1392).

Although *Antrodia camphorata* extracts were reported to have the abovementioned effects from previous experiments, and the components were analyzed in succession, further experiments are needed to identify the effective composition for liver protection. The application in liver diseases treatment and prevention of components from *Antrodia camphorata* extracts will be of great beneficial effects from studies of liver protection if the real effective composition is found.

SUMMARY OF THE INVENTION

In order to identify which are the compounds to prevent or treat liver diseases from the extracts of *Antrodia camphorata*, the compound of the formula (1) was isolated and purified in the present invention,

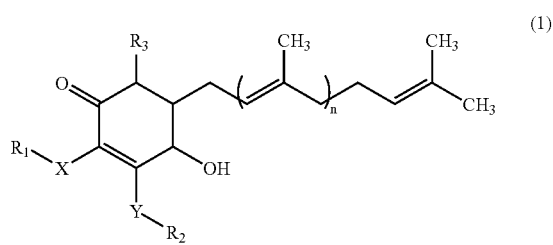

wherein X and Y can be oxygen or sulfur, $R_1$, $R_2$ and $R_3$ are each a hydrogen atom, methyl or $(CH_2)_m—CH_3$ and m=1-12; n=1-12.

A preferred compound of the general formula (1) is 4-hydroxy-2,3-dimethoxy-6-methyl-5(3,7,11-trimethyl-dodeca-2,6,10-trienyl)-cyclohex-2-enone as shown in formula (2), with molecular formula of $C_{24}H_{38}O_4$, appearance of pale yellow powder and molecular weight of 390.

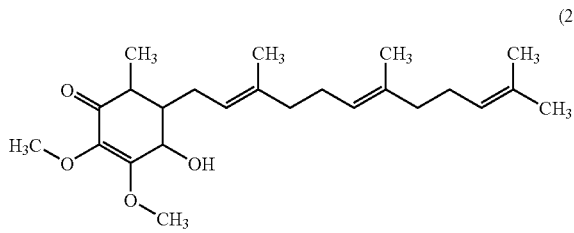

Cyclohexenone compounds having the structures of formula (1) and formula (2) are purified from aqueous extraction or organic solvent extraction of *Antrodia camphorata*. The organic solvents used include, but not limited to, alcohols such as methanol, ethanol or propanol, esters such as ethyl acetate, alkanes such as hexane, or halogenated alkanes such as chloromethane, chloroethane. Among them, alcohol is preferred, and ethanol is particularly preferred.

Cyclohexenone compounds of formula (1) and formula (2) according to the present invention are applied in liver protection and alleviation of liver injury and fibrosis. Feeding cyclohexenone to carbon tetrachloride ($CCl_4$) treated rats helped to alleviate the progress of rat liver injury and fibrosis. The levels of alanine aminotransferase (ALT) and aspartate aminotransferase (AST) were decreased to achieve liver protection ability. In addition, cyclohexenone from *Antrodia camphorata* helped to increase glutathione peroxidase (GSHPx) and antioxidant enzymes catalase (CAT) in the liver in order to decrease the liver cell injury and lower the oxidative pressure induced by free radicals, further to increase antioxidant ability.

On the other hand, the compounds of formula (1) and/or formula (2) in the present invention can be incorporated into pharmaceutical compositions for treating liver injury to improve the symptoms induced by liver injury in mammals such as human. The pharmaceutical compositions include not only the compounds of formula (1) and/or formula (2), but also the pharmaceutically accepted carries. Examples of such carriers include, but are not limited to, excipients such as water, fillers such as sucrose or starch, binders such as cellulose derivatives, diluents, disintegrants, absorption enhancers or sweeteners. The compositions can be manufactured through mixing the compounds of formula (1) and/or formula (2) with at least one of the carriers by means of conventional methods known in the pharmaceutically technical field, which can be formulated in the form of, but are not limited to, powder, tablets, capsules, pellets, granules or other liquid formulation.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

The patent or application file contains at least one drawing executed in color. Copies of this patent or patent application publication with color drawing(s) will be provided by the office upon request and payment of the necessary fee.

DETAILED DESCRIPTION OF THE PREFERRED EMBODIMENT

Figure 1:
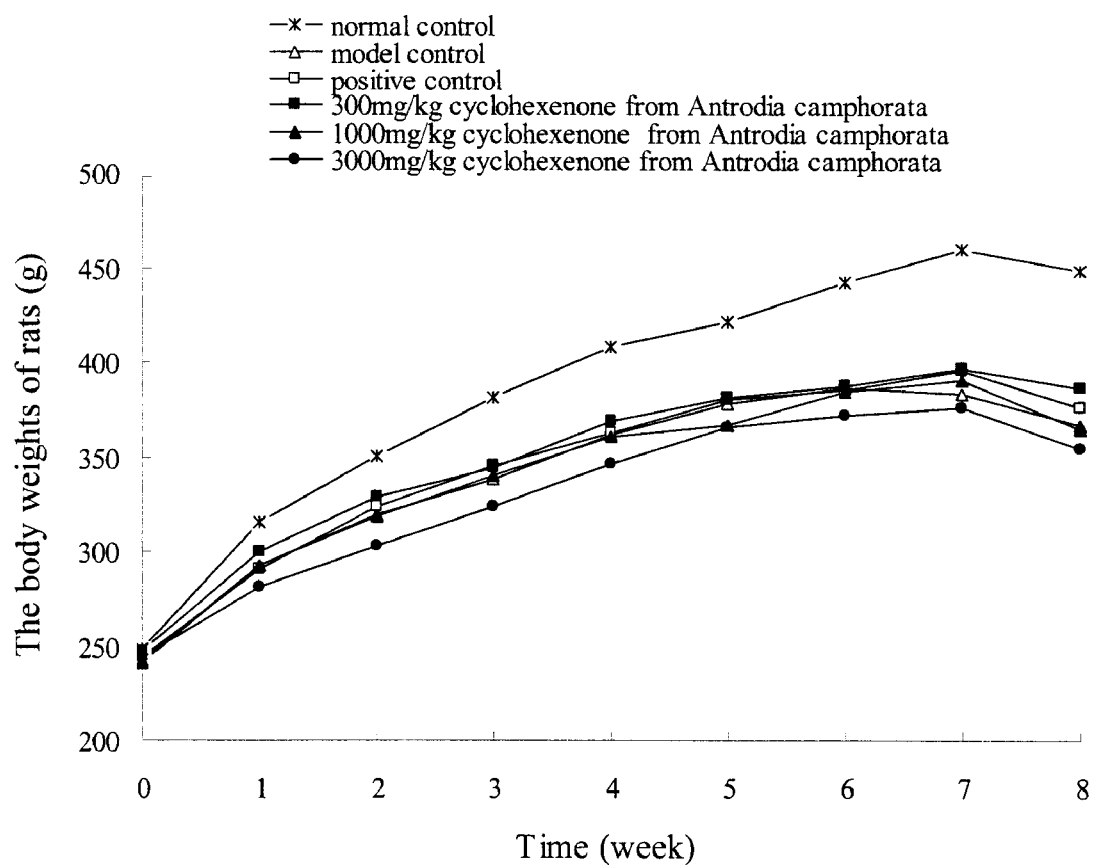
FIG. 1 The body weights of rats from each group. *: normal control (gp. A); □: model control (gp. B, animals receiving 20% $CCl_4$); □: positive control (gp. C, animals receiving 20% $CCl_4$ and silymarin); ■: animals receiving 20% $CCl_4$ and 300 mg/kg cyclohexenone (gp. D); ▲: animals receiving 20% $CCl_4$ and 1000 mg/kg cyclohexenone (gp. E), and ●: animals receiving 20% $CCl_4$ and 3000 mg/kg cyclohexenone (gp. F).

The mycelia, fruiting bodies or mixture of both from *Antrodia camphorata* are first extracted with water or organic solvents to obtain the aqueous extract or organic solvent extract of *Antrodia camphorata* using the methods well known in the arts. The organic solvents include, but not limited to, alcohols such as methanol; ethanol or propanol; esters such as ethyl acetate; alkanes such as hexane; or halogenated alkanes such as chloromethane, and chloroethane. Among them, alcohol is preferred, and ethanol is particularly preferred.

The aqueous or organic solvent extracts of *Antrodia camphorate* were subjected to high-performance liquid chromatography (HPLC) for isolation and purification. Each fraction was recovered and applied to liver protection assay. The potent fractions with liver protective ability were analyzed for the composition and further assayed with related biochemical tests for alleviating liver injury. The above approach then led to the identification of compounds of formula (1) and formula (2) in liver protection by alleviating liver injury.

The compound 4-hydroxy-2,3-dimethoxy-6-methyl-5(3, 7,11-trimethyl-dodeca-2,6,10-trienyl)-cyclohex-2-enone of the formula (2) is explained below as an example for the present invention. Liver protective ability of 4-hydroxy-2,3-dimethoxy-6-methyl-5(3,7,11-trimethyl-dodeca-2,6,10-trienyl)-cyclohex-2-enone were assessed by evaluating the extent of liver injury in liver fibrosis with analysis of the markers of liver injury such as ALT, AST, glutathione (GSH), glutathione peroxidase (GSHPx), catalase (CAT), superoxide dismutase (SOD) after feeding various dosages of cyclohexenone from *Antrodia camphorata* on chronic liver injury of rats induced by carbon tetrachloride.

These assays have proved that 4-hydroxy-2,3-dimethoxy-6-methyl-5(3,7,11-trimethyl-dodeca-2,6,10-trienyl)-cyclohex-2-enone from *Antrodia camphorata* can be used to alleviate liver injury and fibrosis caused by chemicals. The levels of inflammatory markers ALT and AST were decreased, the levels of GSHPx and CAT in the liver were increased in order to decrease the liver cell injury and lower the oxidative pressure induced by free radicals, further to increase antioxidant ability of the liver. The details of the examples are described as follows:

Example 1

Isolation of 4-hydroxy-2,3-dimethoxy-6-methyl-5(3, 7,11-trimethyl-dodeca-2,6,10-trienyl)-cyclohex-2-enone One hundred grams of mycelia, fruiting bodies or mixture of both from *Antrodia camphorata* were placed into a flask. A proper amount of water and alcohol (70-100% alcohol solution) was added into the flask and were stirred at 20-25° C. for at least 1 hour. The solution was filtered through a filter and a 0.45 μm membrane and the filtrate was collected as the extract.

The filtrate of *Antrodia camphorata* was subjected to High Performance Liquid chromatography (HPLC) analysis. The separation was performed on a RP18 column, the mobile phase consisted of methanol (A) and 0.1-0.5% acetic acid (B), with the gradient conditions of 0-10 min in 95%~20% B, 10-20 min in 20%~10% B, 20-35 min in 10%~10% B, 35-40 min in 10%~95% B, at the flow rate of 1 ml/min. The column effluent was monitored with a UV-visible detector.

The fractions collected at 25-30 min were collected and concentrated to yield 4-hydroxy-2,3-dimethoxy-6-methyl-5 (3,7,11-trimethyl-dodeca-2,6,10-trienyl)-cyclohex-2-enone, a product of pale yellow powder. The analysis of 4-hydroxy-2,3-dimethoxy-6-methyl-5 (3,7,11-trimethyl-dodeca-2,6,10-trienyl)-cyclohex-2-enone showed the molecular formula of $C_{24}H_{38}O_4$, molecular weight of 390, melting point of 48° C.~52° C. Investigation of NMR spectra showed that $^1$H-NMR (CDCl$_3$) δ (ppm)=1.51, 1.67, 1.71, 1.75, 1.94, 2.03, 2.07, 2.22, 2.25, 3.68, 4.05, 5.07, and 5.14; $^{13}$C-NMR (CDCl$_3$) δ (Ppm)=12.31, 16.1, 16.12, 17.67, 25.67, 26.44, 26.74, 27.00, 39.71, 39.81, 4.027, 43.34, 59.22, 60.59, 120.97, 123.84, 124.30, 131.32, 135.35, 135.92, 138.05, 160.45, and 197.12.

Example 2

Liver Protection Tests with Cyclohexenone of *Antrodia camphorata*

The main causes for liver disease include virus, alcohol and chemicals. Chemical induced liver injury in rats exhibits consistent features in pathological section of human liver injury. The liver protection assessment in this study is focused on chemical induced liver injury. The effects of cyclohexenone from *Antrodia camphorata* on chronic liver injury of rats were evaluated through the biochemical assays of liver injury and the liver tissue section based on the chronic liver injury model of rats induced by carbon tetrachloride. Carbon tetrachloride ($CCl_4$) causes hepatocellular necrosis, further to fibrosis and cirrhosis if not be withdrawn. The toxicity of carbon tetrachloride is activated in the liver by the cytochrome P-450 system. The initial metabolite is the trichloromethyl radical (.$CCl_3$), which binds with protein to inhibit the protein synthesis, induces imbalanced lipid metabolism with the outcome of triglyceride accumulation. The peroxyl product of .$CCl_3$ induced a lipid peroxidation and damages of cell membrane in the liver, which causes liver enzyme secretion and cell necrosis. As cited above, the animal model of liver injury induced by carbon tetrachloride has similarity to human liver cirrhosis. Therefore, the model can be applied in evaluation of the therapy effects of drugs or food compositions. The details of the procedures are described below.

(1) Establishment of Liver Injury Animal Model Induced by $CCl_4$

The animal model was performed with five-week-old Sprague-Dawley (SD) rats purchased from BioLasco Taiwan Co., Ltd. Healthy rats weighing 220-270 g were chosen for experiment after observing for 2 weeks in the laboratory animal room. The rats were randomly divided into 6 groups (12 rats/group): normal (gp. A); control groups including model control (gp. B) and positive control (gp. C, animals receiving silymarin); treatment groups including animals receiving 300 mg/kg of cyclohexenone (gp. D), 1000 mg/kg of cyclohexenone (gp. E), and 3000 mg/kg of cyclohexenone (gp. F), as indicated in Table 1. Only normal group was not poisoned with $CCl_4$. The body weights were recorded to calculate the dosage. Silymarin, the flavonoid extracted from milk thistle, has been shown to help decrease the liver inflammation and promote healing. It helps to remove toxins from liver cells by either neutralizing the toxicity of toxic compounds or competing with the binding sites in liver. It is a potent antioxidant, protects the liver from free radicals. It has been widely studied for treating various types of liver injury in animals and clinical trials. The beneficial effects on liver protection have made silymarin a good medicine for liver diseases and a drug in positive control group for the animal model of liver injury.

TABLE 1

The experimental groups with the substances fed and the dosages

|  | Group | 20% (v/v) $CCl_4$ | cyclohexenone | silymarin |
| --- | --- | --- | --- | --- |
| Control groups | A (normal) | 0 | 0 | 0 |
|  | B (model control) | 2 ml/kg BW | 0 | 0 |
|  | C (positive control) | 2 ml/kg BW | 0 | 200 mg/kg |
| Treatment group | D | 2 ml/kg BW | 300 mg/kg | 0 |
|  | E | 2 ml/kg BW | 1000 mg/kg | 0 |
|  | F | 2 ml/kg BW | 3000 mg/kg | 0 |

Rats in normal group (group A) were fed with corn oil (Sigma chemical co.) by means of stomach tubes. Carbon tetrachloride (Shimakyu, Osaka, Japan) was administered to groups B to F via stomach tubes twice weekly (every Tuesday and Thursday afternoon) for 8 weeks, at a dose of 2 ml/kg of body weight, diluted with corn oil. Silymarin was prepared with saline in an amount of 200 mg/kg of body weight and was fed to rats of group C via a stomach tube. Cyclohexenone prepared from example 1 was mixed with saline, and fed in the amounts of 300 mg/kg, 1000 mg/kg and 3000 mg/kg of body weight to rats of group D to F via stomach tubes. The total feeding volume was estimated in the ratio of 10 ml/kg of body weight to groups C to F five days a week (every morning) for 8 weeks. The body weights of rats and the amounts of food intake in rats for each group were shown in FIG. 1 and FIG. 2, respectively.

FIG. 1 shows the body weight changes of rats during 8 weeks of experiment in control groups and treatment groups. The weight of rats decreased in all $CCl_4$-treated groups except rats in normal group after one week of experiment though the weights in the beginning were not significantly different among groups. The body weights of rats in model group (gp. B, 366.9 g), were remarkably lower than those in normal group (gp. A, 448.7 g), at the $8^{th}$ week of experiment. The treatment of $CCl_4$ resulted in pathological changes in rats, which caused the decrease of body weight. In addition, rats fed with silymarin (positive control, gp. C) showed a less decrease in weights as low as 375.8 g than rats in model control group (gp. B). The body weights did not drop sharply when silymarin was administered. While rats fed with cyclohexenone from *Antrodia camphorata* in the amount of 300 mg/kg, 1000 mg/kg, and 3000 mg/kg showed weights of 386.6 g, 365.1 g and 355.0 g, respectively. This represented the feeding of cyclohexenone from *Antrodia camphorata* could effectively alleviate the weight decrease situation when receiving cyclohexenone at the amount of as low as 300 mg/kg of body weight.

Figure 2:
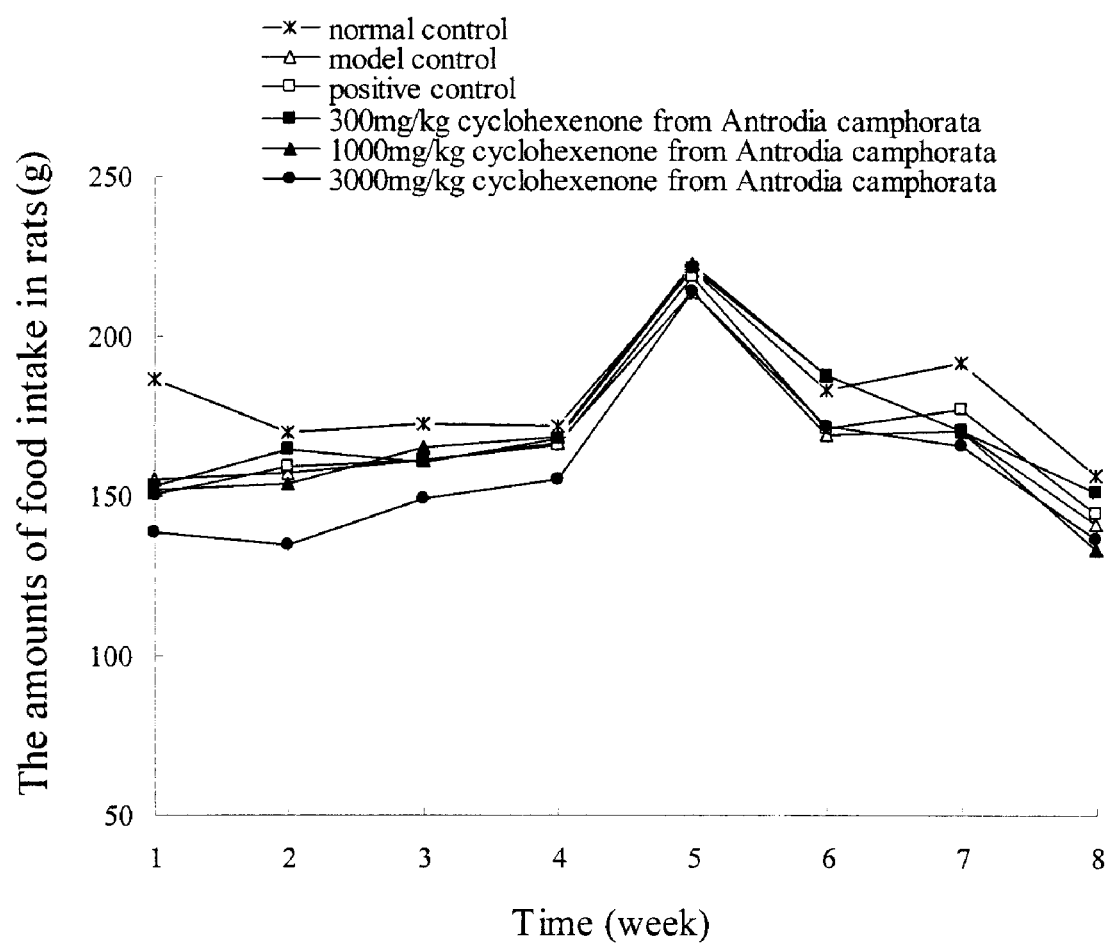
FIG. 2 The amounts of food intake in rats from each group. *: normal control (gp. A); Δ: model control (gp. B, animals receiving 20% $CCl_4$); □: positive control (gp. C, animals receiving 20% $CCl_4$ and silymarin); ▮: animals receiving 20% $CCl_4$ and 300 mg/kg cyclohexenone (gp. D); ▲: animals receiving 20% $CCl_4$ and 1000 mg/kg cyclohexenone (gp. E), and ●: animals receiving 20% $CCl_4$ and 3000 mg/kg cyclohexenone (gp. F).

FIG. 2 shows the amounts of food intake during 8 weeks of experiment in control groups and treatment groups. The food intake increased during the first to the $5^{th}$ week of experiment, while the intake dropped and showed decreasing trends in each group after the $5^{th}$ week. Treatment of $CCl_4$ could affect the food intake.

(2) Effects of $CCl_4$ to the Weights of Liver, Kidney and Spleen

All rats were sacrificed at the end of the $8^{th}$ week of experiment. The weights of liver, kidney and spleen were recovered and weighted and compared with the body weights to calculate the ratios and observe the effects of cyclohexenone from *Antrodia camphorata* to $CCl_4$ treatment. All values are expressed as mean ±SD, which were evaluated using One-way Analysis of Variance. Those with significant differences were further tested with the Least Significant Difference Test (LSD) or Student t-test to compare cyclohexenone treatment groups and normal groups, positive control and model groups. $P<0.05$ was selected as criterion for statistical significance in all cases. The results are shown in Table 2.

TABLE 2

The effect of cyclohexenone from *Antrodia camphorata* to the weights of organs in rats after $CCl_4$-induced liver injury

| Group | spleen (%) | kidney (%) | liver (%) |
|---|---|---|---|
| A (normal) | 0.16 ± 0.03 | 0.62 ± 0.06 | 2.68 ± 0.33 |
| B (model control, 20% $CCl_4$) | 0.25 ± 0.08* | 0.76 ± 0.11* | 3.30 ± 0.54* |
| C (positive control, silymarin) | 0.22 ± 0.05* | 0.71 ± 0.08* | 3.43 ± 0.63* |
| Treatment groups Cyclohexenone from *Antrodia camphorata* (mg/kg) | | | |
| D. 300 mg/kg | 0.20 ± 0.05* | 0.68 ± 0.06* | 3.29 ± 0.35 |
| E. 1000 mg/kg | 0.22 ± 0.06* | 0.69 ± 0.13 | 3.20 ± 0.47* |
| F. 3000 mg/kg | 0.30 ± 0.10* | 0.73 ± 0.08* | 3.65 ± 0.53* |

1) All values were expressed as mean ± SD using MS-Excels program.
*$P < 0.05$, showing a significant difference between normal group and other tested groups after analyzed with Student t-test.
a: $P < 0.05$, showing a significant difference between model group and other tested groups after analyzed with Student t-test.

Each of the liver, spleen, and kidney to body weight ratio (%) from model group is significantly higher than those from the normal group. $CCl_4$ has shown to cause pathological changes in these organs by increasing the weights. The increases from silymarin treated group are less than those of model group since silymarin has liver protective effects. On the other hand, $CCl_4$ treated rats fed with different amount of cyclohexenone from *Antrodia camphorata* showed increase in organ to body weight ratio, but the increases are less than those of model group when the amount of cyclohexenone fed was 300 mg/kg or 1000 mg/kg. These results show beneficial effect of cyclohexenone from *Antrodia camphorata* in $CCl_4$ treated rats since the organ weights were not consistently increased.

(3) Pathological Changes of Liver Tissues

The pathological changes of the liver surface were examined with naked eyes when the liver was taken out from rats, and then tissue sections were made. Half of each liver lobe was stored at –80° C. for antioxidant enzyme assay to follow up. The rest of liver tissues were fixed in 10% formalin for one week, embedded in paraffin cut into 2 μm sections, and stained with Hematoxyline-eosin (H&E) to visualize the lipid deposition, inflammation, cell necrosis and fibrosis, or stained with Masson's trichromic solution to visualize extracellular matrix and collagen fibers for liver fibrosis development. The pathological changes of liver injury were evaluated under light microscope (Opticphot-2, Nikon, Tokyo, Japan) after stained with the abovementioned solution.

Assessment of pathologic score in the chronic liver damage, the extent of inflammation, vacuolar degeneration, liver cell necrosis and bile duct proliferation were graded semi-quantitatively on a "0" to "4" scale (level 0=−, none, level 1=+, slight, level 2=++, mild, level 3=+++, moderate, and level 4=++++, remarkable, according to Jonker et al. (Jonker, A. M., Dijkhuis, F. W., Boes, A., Hardonk, M. J. and Grond J. 1992. Immunohistochemical study of extracellular matrix in acute galactosamine hepatitis in rats. Hepatology. 15(3):423-31).

Liver fibrosis was evaluated semiquantitatively according to the scoring methods from Gabriele et al. (Gabriele, B. 1997. Silymarin retards collagen accumulation in early and advanced biliary fibrosis secondary to complete bile duct obliteration in rats. Hepatology 26: 643-649) and Wang et al. (Wang, G. S., Eriksson, L. C., Xia, L., Olsson, J. and Stal, P. 1999. Dietary iron overload inhibits carbon tetrachloride-induced promotion in chemical hepatocarcinogenesis: effects on cell proliferation, apoptosis, and antioxidation. J. Hepatol. 30(4):689-98.). Fibrosis was staged on a 0-4 scale: level 0, no fibrosis, normal liver tissue; level 1, proliferation of collagen, portal fibrosis without septa (proliferation of radiating fiber in central vein or periportal region); level 2, incomplete septa between central vein and periportal region (septa without bridging); level 3, intact septal fibrosis and bridging, many nodules in liver, the septa is thin; and level 4, complete thick septa, definite cirrhosis. The results are shown in FIG. 3 to FIG. 5, and Table 3.

Figure 3:
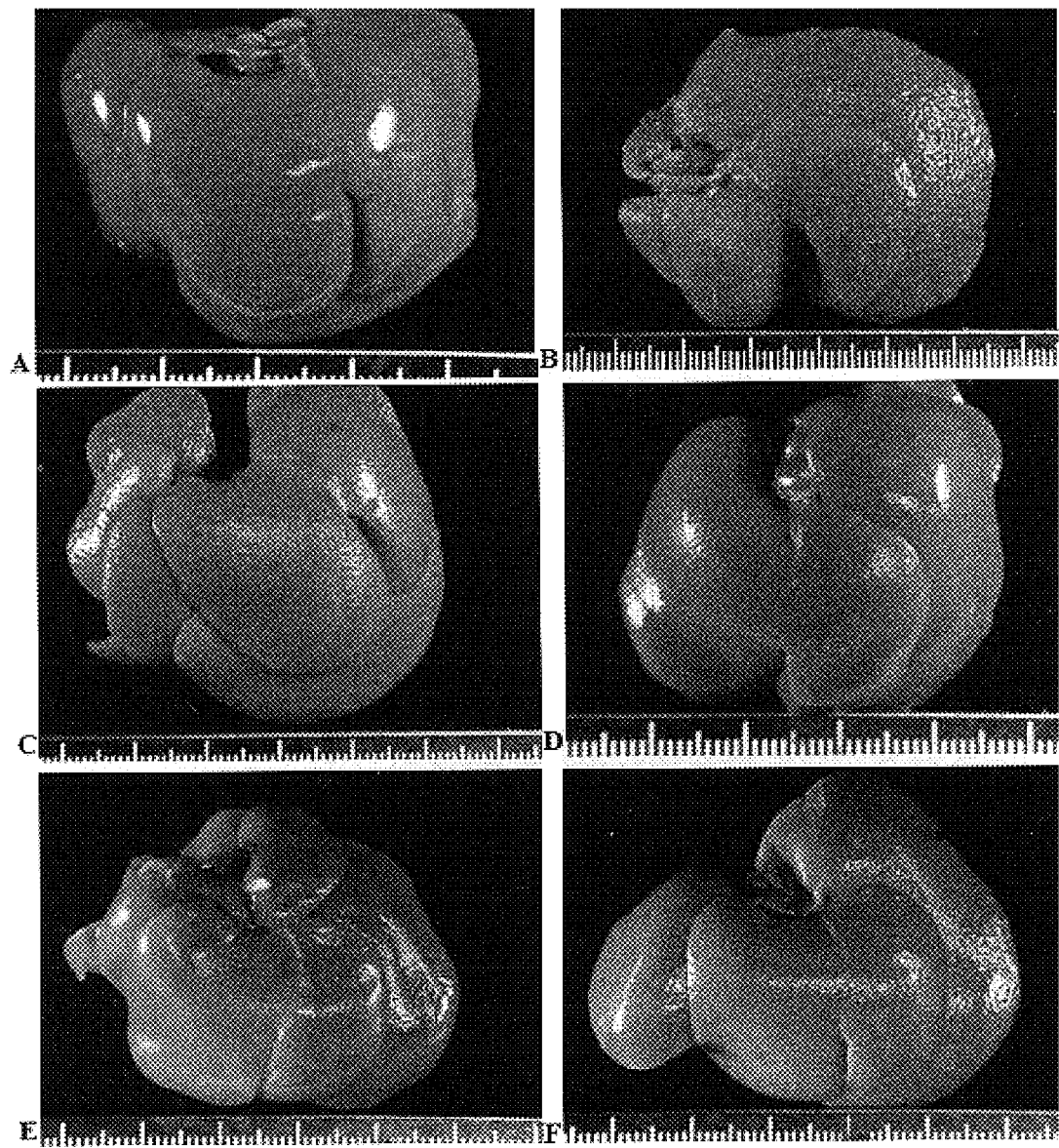
FIG. 3 The pathological changes of the liver surface observed with naked eyes in rats from each group. (A) normal control (gp. A, corn oil only); (B) model control (gp. B, animals receiving 20% $CCl_4$); (C) positive control (gp. C, animals receiving 20% $CCl_4$ and 200 mg/kg silymarin); (D) animals receiving 20% $CCl_4$ and 300 mg/kg cyclohexenone (gp. D); (E) animals receiving 20% $CCl_4$ and 1000 mg/kg cyclohexenone (gp. E), and (F) animals receiving 20% $CCl_4$ and 3000 mg/kg cyclohexenone (gp. F).
Figure 4:
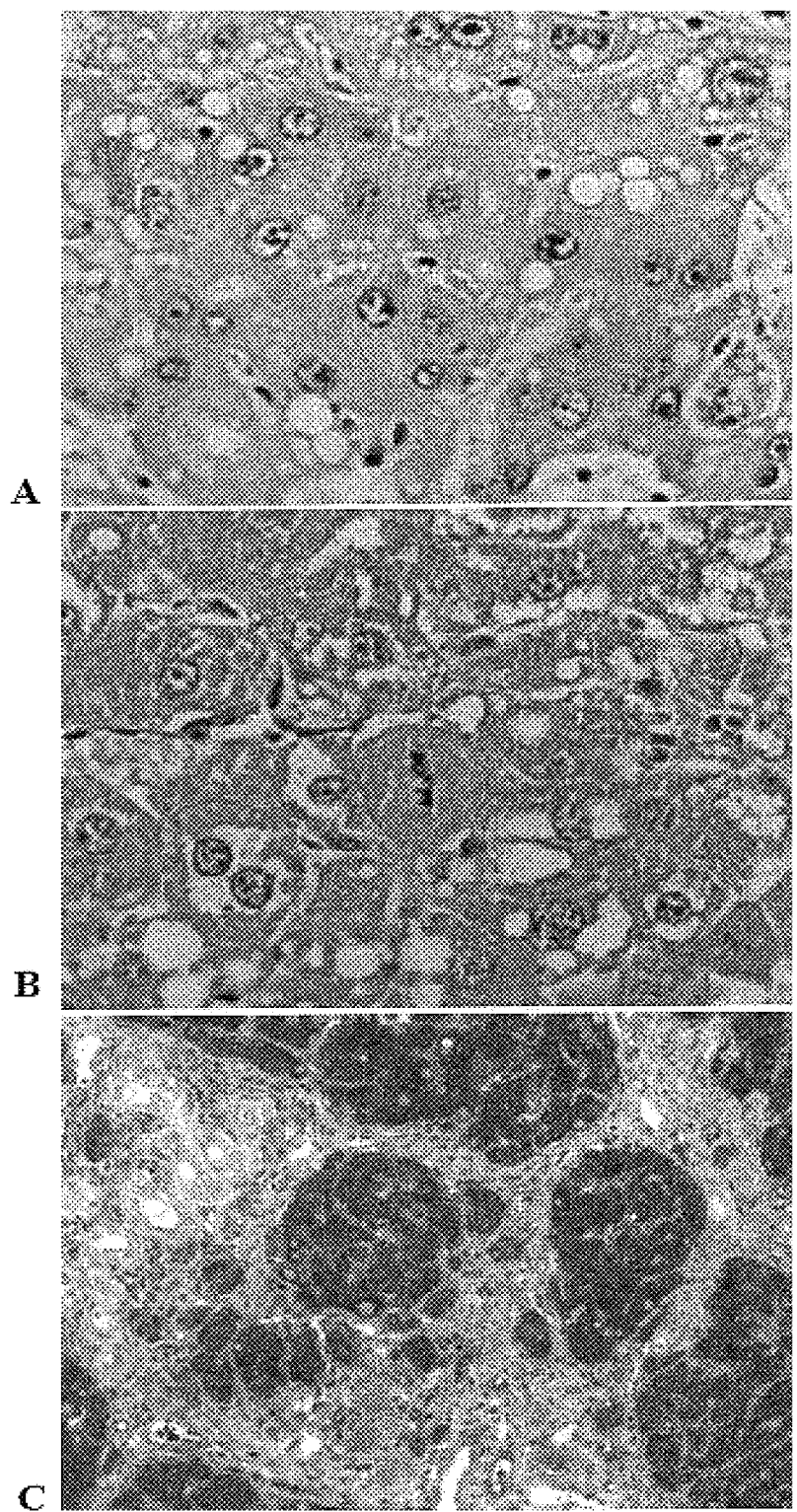
FIG. 4 The pathological changes of $CCl_4$-induced liver injury in rats of the invention. (A) H&E staining, magnified 200-fold; (B) H&E staining, magnified 400-fold; (C) MT staining of collagen fibers, magnified 100-fold, showing vacuoles, fibrosis with nodules, and formation of cirrhosis.

FIG. 3 shows the pathological changes of the liver surface observed with naked eyes from each group. In the normal group, the liver surface was smooth (FIG. 3A); while in the $CCl_4$-treated model group, the liver was yellow in color, with rough, uneven and tough surface and swelling conditions (FIG. 3B). After rats receiving silymarin or various amounts of cyclohexenone from *Antrodia camphorata*, the extents of liver pathological changes were significantly weaker than that of model group (FIG. 3C-FIG. 3F), though showing swelling and pathological conditions. Among them, rats fed with cyclohexenone in the amount of 3000 mg/kg body weight showed the slightest condition in swelling and pathological conditions (FIG. 3F). It shows that cyclohexenone from *Antrodia camphorata* can effectively improve the surface injury symptoms induced by $CCl_4$ in liver surfaces.

300 mg/kg and 1000 mg/kg, mainly distributed in slight to moderate levels with scores of 1.8 and 2.0, respectively.

Figure 5:
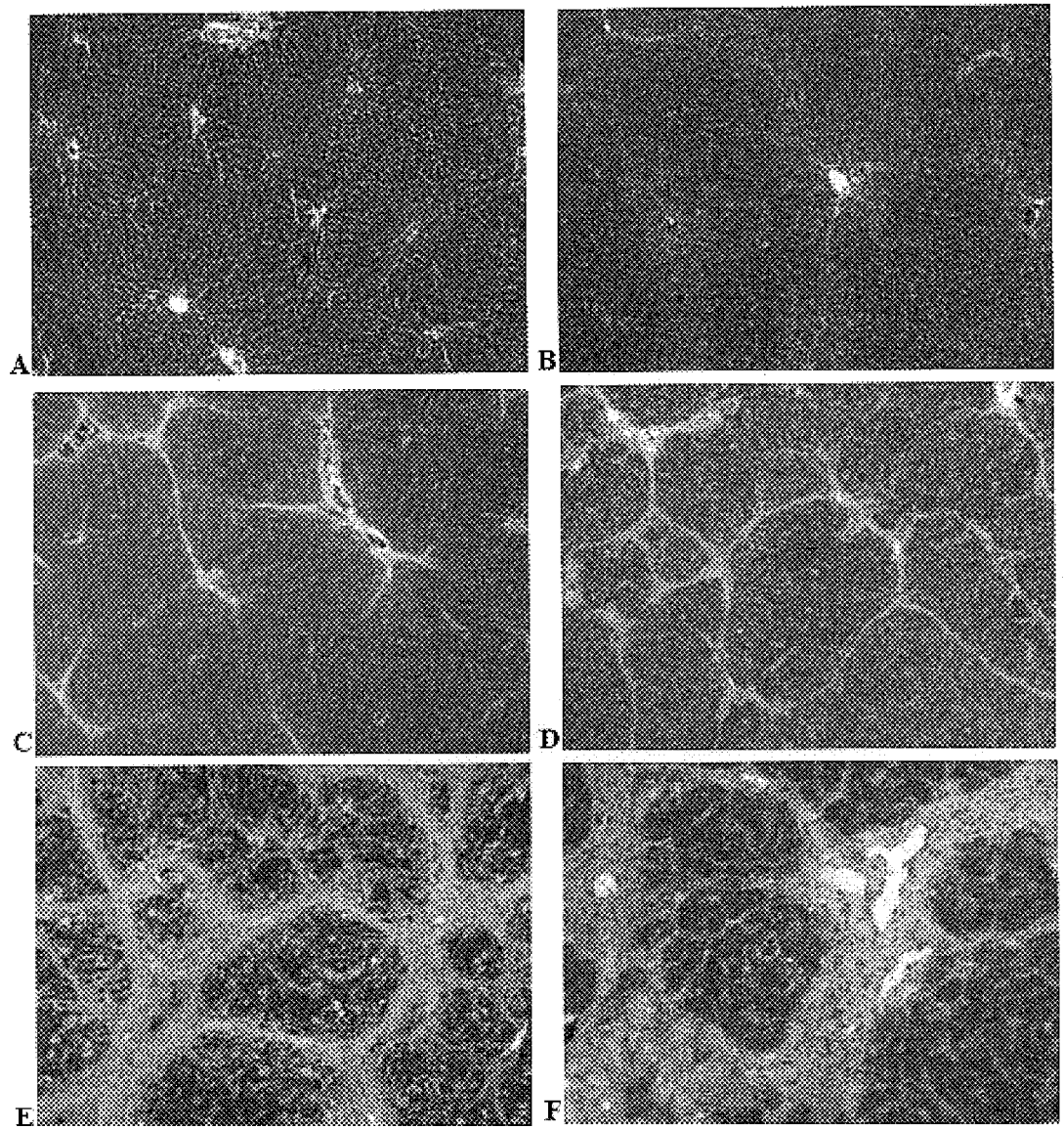
FIG. 5 The pathological changes of liver fibrosis in rats before or after $CCl_4$ induction with MT staining on collagen fibers. (A) normal liver tissue; (B) various extents of liver fibrosis and proliferation of collagen after $CCl_4$ treatment; (C) incomplete septa between central vein and periportal region after $CCl_4$ treatment; (D) intact septal fibrosis and bridging, many nodules in liver, the septa is thin; (E) complete thick septa, definite cirrhosis after $CCl_4$ treatment; (F) liver fibrosis and green collagen after $CCl_4$ treatment. (A) to (E): 40-fold magnification; (F) 100-fold magnification.

Referring to FIG. 5 and Table 3, FIG. 5 shows the pathological changes of $CCl_4$-induced liver fibrosis in rats. Normal liver shows no fibrosis, and belongs to level 0 according to Gabriele et al. (1997) and Wang et al. (1999) (FIG. 5A); while various fibrosis levels were shown after $CCl_4$ induction: level 1, proliferation of collagen, portal fibrosis without septa (proliferation of radiating fiber in central vein or periportal region) (FIG. 5B); level 2, incomplete septa between central vein and periportal region (septa without bridging) (FIG. 5C); level 3, intact septal fibrosis and bridging, many nodules in liver, the septa is thin (FIG. 5D); and level 4, complete thick septa, definite cirrhosis (FIG. 5E). The collagen in liver appeared to be green after Masson's trichrome staining (FIG. 5F). The liver of the model group showed the most serious liver fibrosis condition, mainly in level 3 and level 4 with a score of 3.2 (Table 3). Silymarin on $CCl_4$ induced liver fibrosis had a score of 2.8, while the extents of liver fibrosis in all treatment groups fed with various amounts of cyclohexenone from *Antrodia camphorata* were improved. The remarkable effect was shown on the dosage of 300 mg/kg, mainly distributed in level 1 to level 2 with a score of 1.8.

TABLE 3

Histological evaluation of $CCl_4$ induced liver injury in rats from different group

| Group | Liver injury | | | | | | Liver fibrosis | | | | | |
|---|---|---|---|---|---|---|---|---|---|---|---|---|
| | − | + | ++ | +++ | ++++ | score | − | + | ++ | +++ | ++++ | score |
| A (normal) | 12[5)] | — | — | — | — | 0.0 | 12 | — | — | — | — | 0.0 |
| B (model control, 20% $CCl_4$) | — | — | 2 | 3 | 4 | 3.2* | — | — | 2 | 3 | 4 | 3.2* |
| C (positive control, silymarin) | — | 2 | 1 | 4 | 3 | 2.8* | — | 2 | 1 | 5 | 3 | 2.8* |
| Treatment groups Cyclohexenone from *Antrodia camphorata* (mg/kg) | | | | | | | | | | | | |
| D. 300 mg/kg | — | 5 | 6 | — | 1 | 1.8*[a] | — | 6 | 4 | 1 | 1 | 1.8*[a] |
| E. 1000 mg/kg | — | 3 | 6 | 1 | 1 | 2.0*[a] | 2 | 1 | 4 | 3 | 1 | 2.0*[a] |
| F. 3000 mg/kg | — | 2 | 6 | 1 | 2 | 2.3*[a] | — | 2 | 4 | 3 | 2 | 2.5* |

1) Assessment of pathologic score in the chronic liver damage, the extent of inflammation, vacuolar degeneration, liver cell necrosis and bile duct proliferation were graded semi-quantitatively according to Jonker et al. 1992 on a "0" to "4" scale (level 0 = −, none, level 1 = +, slight, level 2 = ++, mild, level 3 = +++, moderate, and level 4 = ++++, remarkable).
2) Chronic liver injury score in rats = counts of pathological rats/total counts of rats.
3) Fibrosis was staged according to Gabriele et al. (1997) and Wang et al. (1999) on a 0-4 scale: level 0, no fibrosis, normal liver tissue; level 1, proliferation of collagen, portal fibrosis without septa (proliferation of radiating fiber in central vein or periportal region); level 2, incomplete septa between central vein and periportal region (septa without bridging); level 3, intact septal fibrosis and bridging, many nodules in liver, the septa is thin; and level 4, complete thick septa, definite cirrhosis.
4) Liver fibrosis score in rats = counts of pathological rats/total counts of rats.
[5)]Counts of pathological rats.
*$P < 0.05$, showing a significant difference between normal group and other tested groups after analyzed with Student t-test.
[a]$P < 0.05$, showing a significant difference between model group and other tested groups after analyzed with Student t-test.

Referring to FIG. 4 and Table 3, FIG. 4 shows the pathological changes of liver injury induced by $CCl_4$. The liver was swollen in tissue sections, with abundant mitotic division and increased numbers of Kuffer cells (FIG. 4A and FIG. 4B). Vacuoles appeared, many nodules were found, and resulted in liver cirrhosis in serious conditions (FIG. 4C). The liver of the model group showed obvious and the most serious liver injury condition, mainly in moderate to remarkable levels with a score of 3.2 according to Jonker et al. (Table 4). Silymarin on $CCl_4$ induced liver injury had a score of 2.8, while the extents of liver injury in all treatment groups fed with various amounts of cyclohexenone from *Antrodia camphorata* were improved. The remarkable effects were shown in dosages of These results show beneficial effects of cyclohexenone from *Antrodia camphorata* in $CCl_4$ treated rats in liver injury and liver fibrosis. $CCl_4$ treated rats fed with different amount of cyclohexenone from *Antrodia camphorata* all showed better effects than silymarin. And the best effect was found on the dosage of 300 mg/kg.

(4) Indicators of Liver Function

Alanine aminotransferase (ALT) and aspartate aminotransferase (AST) are important enzymes in amino acid synthesis for human organs such as liver, heart, muscle and the like. These enzymes maintain low contents in serum under normal condition with levels of 40 U/L for ALT and 50 U/L for AST. The increase in serum ALT and AST release are associated with inflammation of cells from the abovementioned organs, which are caused by the change of cell permeability or cell rupture. Therefore the levels of ALT and AST are good indicators for liver inflammation and liver injury.

All rats were sacrificed at the end of the 8th week of experiment, blood samples were collected from abdominal aorta for assessing liver biochemical parameters. Five ml of blood were transferred to a tube and centrifuged at 775×g for 15 min. 0.5 ml of serum was analyzed on an Express plus automatic clinical chemistry analyzer (Chiron diagnostics corporation, OH, USA) with commercial kits of ALT (Bayer diagnostics, Cat No. E36941), AST (Bayer diagnostics, Cat No. E37041) and cholesterol (Bayer diagnostics, Cat No. E33940). All values are expressed as mean ±SD, which were evaluated using One-way Analysis of Variance. Those with significant differences were further tested with the Least Significant Difference Test (LSD) or Student t-test to compare cyclohexenone treatment groups and normal groups, positive control and model groups. $P<0.05$ was selected as criterion for statistical significance in all cases. The results are shown in Table 4.

TABLE 4

Indicators of liver function of $CCl4$ induced liver injury in rats from different group

| Group | ALT (U/L) | AST (U/L) | Cholesterol (mg/dL) |
|---|---|---|---|
| A (normal) | 50.7 ± 9.11) | 110.9 ± 25.1 | 63.8 ± 12.2 |
| B (model control, 20% $CCl_4$) | 453.4 ± 201.8* | 470.4 ± 310.1* | 66.7 ± 8.7 |
| C (positive control, Silymarin) | 180.8 ± 94.6* a | 249.5 ± 105.0* a | 69.5 ± 14.3 |
| Treatment groups Cyclohexenone from *Antrodia camphorata* (mg/kg) | | | |
| D. 300 mg/kg | 226.6 ± 138.7* a | 323.4 ± 189.0* | 63.7 ± 15.1 |
| E. 1000 mg/kg | 181.7 ± 78.4* a | 283.2 ± 144.2* | 69.6 ± 14.8 |
| F. 3000 mg/kg | 206.0 ± 98.4* a | 311.7 ± 99.6* | 62.1 ± 16.2 |

1) All values were expressed as mean ± SD using MS-Excels program.
*$P < 0.05$, showing a significant difference between normal group and other tested groups after analyzed with Student t-test.
a: $P < 0.05$, showing a significant difference between model group and other tested groups after analyzed with Student t-test.

The levels of ALT, AST and cholesterol in the $CCl_4$-treated model group were all higher than those in the normal group. $CCl_4$ has shown to cause liver injury, which led to the increase in enzyme activities. The cholesterol level also increased but not much. The increases in ALT, AST and cholesterol from silymarin fed positive control group are less than those of model group since silymarin has liver protective effects. On the other hand, $CCl_4$ treated rats fed with different amount of cyclohexenone from *Antrodia camphorata* showed higher levels in ALT, AST and cholesterol than those of normal group, but the increases are all significantly less than those of model group ($p<0.05$). The decreases of ALT and AST in comparison to the model group in the 1000 mg/kg cyclohexenone treatment group were the most obvious (ALT: 181.7±78.4 U/L, and AST: 283.2±144.2 U/L). These results show that 300 mg/kg, 1000 mg/kg and 3000 mg/kg cyclohexenone from *Antrodia camphorata* can effectively decrease the release of ALT and AST on $CCl_4$ treated rats.

(5) Antioxidant Enzymes in Liver

Antioxidant enzyme system including glutathione (GSH), glutathione peroxidase (GSHPx), catalase (CAT), superoxide dismutase (SOD) and the like plays a great role in protecting organisms from oxidative damage and decrease oxidative stress when free radicals increase. This experiment detected the contents of antioxidant enzymes after $CCl_4$ induced liver injury in rats and evaluated the antioxidant ability of cyclohexenone from *Antrodia camphorata*.

The liver stored at −80° C. as described above was immersed in PBS buffer (phosphate buffered saline solution, pH 7.4) containing 0.16 mg/ml heparin. Red blood cells were removed from the tissue. Liver was prepared as 1.0 g tissue/10 mL buffer homogenates in fresh, chilled 50 mM phosphate, 1 mM EDTA (pH 6-7) buffer using a Polytron homogenizer (setting 5, PT 10 probe, Brinkmann Instruments, Westbury, N.Y.) for one min. The solution was centrifuged at 10,000×g for 15 min at 4° C. Protein concentration was determined with a BCA protein assay kit (Pierce, Ill., USA) at 550 nm using an enzyme linked immunosorbent assay (ELISA) reader (MAX ELISA Reader, Quant, Bio-Tek Instrument, Vermont, USA). Commercial kits of glutathione (GSH), glutathione peroxidase (GSHPx), catalase (CAT), superoxide dismutase (SOD) (Glutathione Assay Kit, Cat No. 703002; Glutathione Peroxidase Assay Kit, Cat No. 703102; Catalase Assay Kit, Cat No. 707002; Superoxide Dismutase Assay Kit, Cat No. 706002) were purchased from Cayman Chemical Company (MI.USA) and assayed by reading at 405 nm, 340 nm, 540 nm and 450 nm using an ELISA reader. Deprotein step was carried out for all the assays mention above except SOD assay. Proteins were precipitated by mixing with equal volume of 10% metaphosphoric acid (w/v), vortex-mixed evenly, centrifuged at 2,000×g for 2 min. The supernatant was removed for enzyme assay. All values are expressed as mean ±SD, which were evaluated using One-way Analysis of Variance. Those with significant differences were further tested with the Least Significant Difference Test (LSD) or Student t-test to compare cyclohexenone treatment groups and normal groups, positive control and model groups. $P<0.05$ was selected as criterion for statistical significance in all cases. The results are shown in Table 5.

TABLE 5

Effects of cyclohexenone from *Antrodia camphorata* on antioxidant enzymes to the $CCl_4$ treated, liver injury model animals

| Group | GSH (uM/mg protein) | GSHPx (nmol/ min/ml) | Catalase (U/mg protein) | SOD (U/ mg protein) |
|---|---|---|---|---|
| A (normal) | 31.5 ± 3.8[1] | 11.4 ± 2.8 | 8.9 ± 1.4 | 0.65 ± 0.22 |
| B (model control, 20% $CCl_4$) | 31.5 ± 6.5 | 9.9 ± 2.5 | 9.6 ± 1.6 | 0.80 ± 0.41 |
| C (positive control, Silymarin) | 30.5 ± 4.1 | 9.6 ± 3.0 | 9.2 ± 1.4 | 0.68 ± 0.23 |
| Treatment groups Cyclohexenone from *Antrodia camphorata* (mg/kg) | | | | |
| D. 300 mg/kg | 30.3 ± 3.2 | 9.6 ± 1.7 | 9.1 ± 1.0 | 0.47 ± 0.17*a |
| E. 1000 mg/kg | 25.2 ± 1.8*a | 11.2 ± 3.4 | 10.1 ± 1.4* | 0.52 ± 0.28 |
| F. 3000 mg/kg | 26.7 ± 4.3*a | 10.6 ± 3.1 | 9.8 ± 0.9 | 0.73 ± 0.23 |

GSH: Glutathione activity (uM/mg protein);
GSHPx: glutathione peroxidase activity (nmol/min/ml) one unit is defined as the amount of enzyme that will cause the oxidation of 1 nmol of NADPH to $NADPH^+$ per minute at 25° C.; Catalase and SOD:U/mg protein
[1]All values were expressed as mean ± SD using MS-Excels program.
*$P < 0.05$, showing a significant difference between normal group and other tested groups after analyzed with Student t-test.
a$P < 0.05$, showing a significant difference between model group and other tested groups after analyzed with Student t-test.

Referring to Table 5, the levels of antioxidant enzymes in the $CCl_4$-treated model group were not significant different from those in the normal group; the levels in silymarin fed positive control group were also not significant different from those either in the normal group or in the model group. Relatively, the SOD level in group D (the 300 mg/kg cyclohexenone fed group) were significantly lower than all other groups. The GSHPx and CAT levels in group E (the 1000 mg/kg cyclohexenone fed group) and F group (the 3000 mg/kg cyclohexenone fed group) were higher than other groups. Both the GSHPx and CAT are able to decompose hydrogen peroxide to non-toxic water to prevent the damage caused by peroxides. Therefore cyclohexenone from *Antrodia camphorata* can decrease the damage of free radicals, reduce the oxidative pressure further to enhance the antioxidant ability by increasing the contents of GSHPx and CAT.

In summary, the compound 4-hydroxy-2,3-dimethoxy-6-methyl-5(3,7,11-trimethyl-dodeca-2,6,10-trienyl)-cyclohex-2-enone isolated from *Antrodia camphorata* according to the present invention can be used to effectively decrease the extents of liver injury and liver fibrosis induced by chemicals. The inflammation indicators of ALT and AST were also reduced. By increasing the contents of GSHPx and CAT, cyclohexenone further decreases the liver damage and the oxidative pressure caused by free radicals, enhances the antioxidant ability and achieves the purposed of liver protection. On the other hand, cyclohexenone from *Antrodia camphorata* is a natural extract, which won't induce uncomfortable side effects, toxicity or complications when applied in treating liver injury or liver protection. It also contains anti-free radical function such as anti-peroxides, which makes it beneficial to human health by preventing liver injury when prepared as health supplements, drinks and the like. In addition, it can be incorporated into pharmaceutical compositions. The pharmaceutical compositions include not only the active compound 4-hydroxy-2,3-dimethoxy-6-methyl-5(3,7,11-trimethyl-dodeca-2,6,10-trienyl)-cyclohex-2-enone, but also the pharmaceutically accepted carries. Examples of such carriers include, but are not limited to, excipients such as water, fillers such as sucrose or starch, binders such as cellulose derivatives, diluents, disintegrants, absorption enhancers or sweeteners. The pharmaceutical composition can be manufactured through mixing the compound of cyclohexenone from *Antrodia camphorata* with at least one of the carriers by means of conventional methods known in the pharmaceutically technical field, which can be formulated in the forms of powder, tablets, capsules, pellets, granules or other liquid formulation, but are not limited to. The purpose for prevention and treatment of liver injury and liver protection can then be accomplished.

What is claimed is:

1. A method for liver protection from chemically induced injury which comprises
administering to a subject in need thereof an effective amount of a cyclohexenone compound of *Antrodia camphorata* having the following formula:

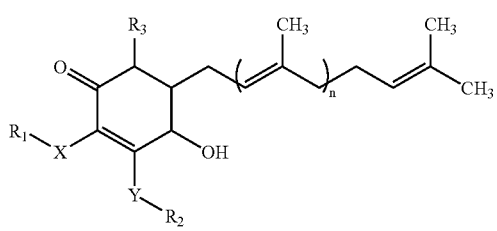

wherein X and Y is oxygen or sulfur, $R_1$, $R_2$ and $R_3$ are each a hydrogen atom, methyl or $(CH_2)_m$—$CH_3$, and m=1-12; n=1-12.

2. The method as claimed in claim 1, wherein the compound is isolated from the organic solvent extracts of *Antrodia camphorate*.

3. The method as claimed in claim 2, wherein the organic solvents are selected from the group consisting of alcohols, esters, alkanes, and halogenated alkanes.

4. The method as claimed in claim 3, wherein the alcohol is ethanol.

5. The method as claimed in claim 1, wherein the compound is isolated from the aqueous extracts of *Antrodia camphorate*.

6. The method as claimed in claim 1, wherein the compound is 4-hydroxy-2,3-dimethoxy-6-methyl-5(3,7,11-trimethyl-dodeca-2,6,10-trienyl)-cyclohex-2-enone.

7. The method according to claim 1, wherein the compound can alleviate liver injury and fibrosis in mammals.

8. The method according to claim 6, wherein the compound can alleviate liver injury and fibrosis in mammals.

9. The method as claimed in claim 7, wherein the amount of the compound to be administered is in the range of 300-3000 mg/kg body weight.

10. The method as claimed in claim 8, wherein the amount of the compound to be administered is in the range of 300-3000 mg/kg body weight.

11. The method as claimed in claim 7, wherein the mammal is a human.

12. The method as claimed in claim 8, wherein the mammal is a human.

13. The method as claimed in claim 7, wherein the liver injury is caused by chemical compounds.

14. The method as claimed in claim 8, wherein the liver injury is caused by chemical compounds.

15. The method as claimed in claim 13, wherein the chemical compound is carbon tetrachloride ($CCl_4$).

16. The method as claimed in claim 14, wherein the chemical compound is carbon tetrachloride ($CCl_4$).

17. The method as claimed in claim 7, wherein the compound protects liver by inhibiting the levels of alanine aminotransferase (ALT) and aspartate aminotransferase (AST).

18. The method as claimed in claim 8, wherein the compound protects liver by inhibiting the levels of alanine aminotransferase (ALT) and aspartate aminotransferase (AST).

19. The method as claimed in claim 7, wherein the compound alleviates the liver injury induced by free radicals through increasing the levels of glutathione peroxidase (GSHPx) and catalase (CAT).

20. The method as claimed in claim 8, wherein the compound alleviates the liver injury induced by free radicals through increasing the levels of glutathione peroxidase (GSHPx) and catalase (CAT).

* * * * *

UNITED STATES PATENT AND TRADEMARK OFFICE
CERTIFICATE OF CORRECTION

PATENT NO. : 7,456,225 B1  Page 1 of 1
APPLICATION NO. : 11/902599
DATED : November 25, 2008
INVENTOR(S) : Sheng-Yun Liu et al.

It is certified that error appears in the above-identified patent and that said Letters Patent is hereby corrected as shown below:

At column 2, lines 50-60, Claim 1, Formula (1) should be corrected to:

(1)

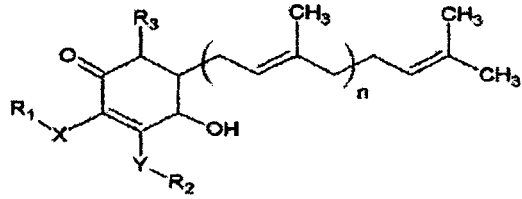

Claim 1, at column 13, lines 53-62, the formula should be corrected to:

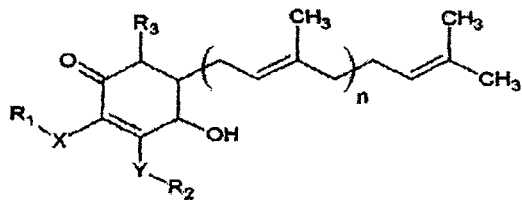

Signed and Sealed this
Twelfth Day of April, 2011

David J. Kappos
*Director of the United States Patent and Trademark Office*